(12) United States Patent
Nyholm

(10) Patent No.: US 8,452,614 B2
(45) Date of Patent: May 28, 2013

(54) DATA ARRANGEMENT, METHOD, DENTAL-CARE-RELATED DEVICE AND SOFTWARE PRODUCT FOR DENTAL-CARE QUALITY ASSURANCE

(75) Inventor: Kustaa Nyholm, Siuntio (FI)

(73) Assignee: Planmeca Oy, Helsinki (FI)

( * ) Notice: Subject to any disclaimer, the term of this patent is extended or adjusted under 35 U.S.C. 154(b) by 1004 days.

(21) Appl. No.: 10/599,506

(22) PCT Filed: Apr. 1, 2005

(86) PCT No.: PCT/FI2005/000172
§ 371 (c)(1),
(2), (4) Date: Aug. 13, 2007

(87) PCT Pub. No.: WO2005/096177
PCT Pub. Date: Oct. 13, 2005

(65) Prior Publication Data
US 2008/0120137 A1 May 22, 2008

(30) Foreign Application Priority Data
Apr. 2, 2004 (FI) .................................... 20045116

(51) Int. Cl.
*G06Q 50/00* (2012.01)
(52) U.S. Cl.
USPC .................................... 705/3; 705/2; 606/170
(58) Field of Classification Search
USPC ........... 705/2, 3; 606/170; 235/375; 204/237; 433/27, 98, 215
See application file for complete search history.

(56) References Cited

U.S. PATENT DOCUMENTS

| | | | |
|---|---|---|---|
| 5,453,009 A * | 9/1995 | Feldman | 433/215 |
| 5,807,521 A * | 9/1998 | Franetzki | 422/20 |
| 6,017,354 A * | 1/2000 | Culp et al. | 606/170 |
| 6,092,722 A * | 7/2000 | Heinrichs et al. | 235/375 |
| 6,117,285 A * | 9/2000 | Welch et al. | 204/237 |
| 6,506,050 B1 * | 1/2003 | Steddin | 433/98 |
| 6,582,225 B1 | 6/2003 | Bergersen | |

(Continued)

FOREIGN PATENT DOCUMENTS

| | | |
|---|---|---|
| DE | 10045067 | 4/2002 |
| FR | 2840091 | 11/2003 |

(Continued)

OTHER PUBLICATIONS

Google Patents search, Jan. 23, 2013.*

(Continued)

*Primary Examiner* — Dilek B Cobanoglu
(74) *Attorney, Agent, or Firm* — Cozen O'Connor

(57) ABSTRACT

The invention relates to a data arrangement in connection with dental care, which arrangement includes at least one dental-care device (U, T) and a data system (S). In the arrangement, information related to a predetermined dental treatment event performed by the dental care device (U, T) is transmitted and stored in the data system (S), such as data of device parameters, instruments (X) or filling material (Y) or time used in the procedure. In the arrangement, the treatment event may be identified, for example, via the control system of the dental-care device (U, T) or by reading an identifier by means of an electronic reader device (L1, L2). The information related to the dental procedure is stored in the data system (S) patient-, instrument- or material-specifically so that it may be utilised afterwards, in case required.

18 Claims, 8 Drawing Sheets

U.S. PATENT DOCUMENTS

| | | | |
|---|---|---|---|
| 7,258,546 B2 * | 8/2007 | Beier et al. ................... | 433/27 |
| 7,739,125 B2 * | 6/2010 | Sorensen et al. ................ | 705/2 |
| 2004/0008123 A1 | 1/2004 | Carrender et al. | |
| 2004/0220836 A1 | 11/2004 | Doherty et al. | |

FOREIGN PATENT DOCUMENTS

| | | |
|---|---|---|
| JP | 2001344338 | 12/2001 |
| JP | 2002282200 | 10/2002 |
| JP | 20030016198 | 1/2003 |
| JP | 2004013837 | 1/2004 |
| JP | 2004-78705 A | 3/2004 |
| WO | WO 01/80117 A1 | 10/2001 |
| WO | 03/071943 | 9/2003 |

OTHER PUBLICATIONS

Smart Medicine, The Application of Audio-ID Technology to Healthcare, David L. Brock, Audio-ID Center, Feb. 1, 2002, 13 pages.

Wireless Telemedicine Systems: An Overview, C.S. Pattichis et al., IEEE Antenna's and Propagation Magazine, vol. 44, No. 2, Apr. 2002, 11 pages.

* cited by examiner

| Hygienist | Dentist | Steriliser | Data system | Dental unit | Stock control |
|---|---|---|---|---|---|

O r d e r

Fetching material package Y

Identifying package Y
                                                    Message to data system "Package Y taken to use"
                                                    Reading data of package Y from data system
                                                    Possible warning of out-of-date material
                                                    Possible automatic setting of instrument parameters o f

Uses light-curing instrument
                                                    Message to data system "Package Y used"

p r o c e d u r e s

Entering "Tooth H of patient P filled with material from package Y" in database
                               Message to stock control "Material Y used"
                                                                               Updating stock balance
                                                                                       Possible automatic order Enters treatment performed and signs entries digitally
                                 Entering data of treatment event and its signature in database Checking out of patient P
                                 Entering data "Treatment of patient P ended at the point of time T3" in database

*Figure 6b*

DATA ARRANGEMENT, METHOD, DENTAL-CARE-RELATED DEVICE AND SOFTWARE PRODUCT FOR DENTAL-CARE QUALITY ASSURANCE

FIELD OF INVENTION

The invention relates to a data arrangement for dental-care environment and especially to storing and transmitting dental-care-related data in connection with dental-care equipment.

PRIOR ART

In connection with dental care, data of, inter alia, patients, materials used in care and/or updates of patient care history are typically registered. Electronic databases enable convenient archiving of data compared to patient indexes on paper. It is easy to handle data afterwards in electronic format and one is able to check what kind of treatment a patient has received. It is also easy to transfer data between clinics, for example, when a patient requires certain treatment the other dental clinic has not been able to offer or when a patient starts using services of a new dentist.

A problem in applying an electronic data system is that someone has to make the required register entries and updates in the database. Manual data entry takes time, and errors may occur in entering and updating. In the dental-care environment, systematic data entry during each treatment stage or immediately after the treatment stage is rarely possible, but one may have to first make temporary notes, whereupon the actual data entry will be made after the patient has left. The possibility of entry errors grows when data is handled manually possibly many times and especially if data is entered afterwards only by heart. Faultless data entry requires, in addition, that the registrar of data knows which data to enter, in which format and whereto. Furthermore, for example capturing of many operation parameters of a dental unit during treatment would require such special arrangements, which are not possible for practical reasons. Thus, treatment histories are typically such that based on them it is practically impossible to establish afterwards and with certainty what treatment the patient was actually given and how. It is essential from the viewpoint of dental-care quality that proper materials and instruments are used in dental procedures, that the instruments are properly cleaned or sterilised, and that they are used in a proper way. This kind of data is not typically entered to the treatment history, let alone such data would be entered so that one could trust or at least assume that the data corresponds to what was actually done.

SUMMARY OF INVENTION

The object of the invention is thus to develop a method and an apparatus implementing the method in order to solve at least some of the abovementioned problems. The object of the invention is achieved by an arrangement, a method, a dental-care device and a software product which are characterised by what is said in the independent patent claims. The advantageous embodiments of the invention are subjects of the dependent claims.

A solution according to the invention is based on a data arrangement in a dental-care environment, which comprises a dental-care-related device and a data system. According to the invention, data transmission communication is arranged between the dental-care-related device and the data system. In the invention, the dental-care-related device identifies procedures performed by it. When the dental-care-related device has identified a procedure, data of the procedure in question is transmitted from the device to the data system as a response to identifying the procedure. The data is stored in the data system to the object of the procedure in question object-specifically.

An advantage of the solution according to the invention is, inter alia, that one may store information related to individual dental sessions more extensively and in more detail. By means of it, it is possible to establish afterwards which treatment the patient was given, how it was given and by which equipment. Thus, a dental clinic can show, if required, that no malpractice has occurred, whereby the possible malpractice accusations may be resolved. When information related to dental care is stored in the data system quickly and reliably already during treatment, one achieves better quality assurance of dental care than before. Because of the invention, data related to the different stages of dental care work may be stored more extensively and in more detail than conventionally has been done. It is advantageous from the viewpoint of the dentist that there is at his/her disposal detailed data in electronic format which is easily processable and from which one may verify how the treatment stages have been carried out. This is advantageous also for patient safety, and legal protection of the dentist and the patient if problems occur in the treated teeth after the treatment.

SUMMARY OF FIGURES

The invention is now described in more detail in connection with preferable embodiments by referring to the accompanying drawings in which:

FIG. 6b shows a table illustrating a method according to an embodiment of the invention.

DETAILED SPECIFICATION OF INVENTION

Preferable embodiments of the invention are described in the following by referring to FIGS. 1, 2, 3, 4, and 5. However, the purpose is not to limit the invention to these embodiments only. The invention may be applied in any dental-care environment in which electronic data entry is required. For this reason, the terms and expressions should be interpreted as broadly as possible as their function is to describe, not to limit the invention. The function is essential from the viewpoint of the invention, not in which device or network element the function is performed.

Figure 1:
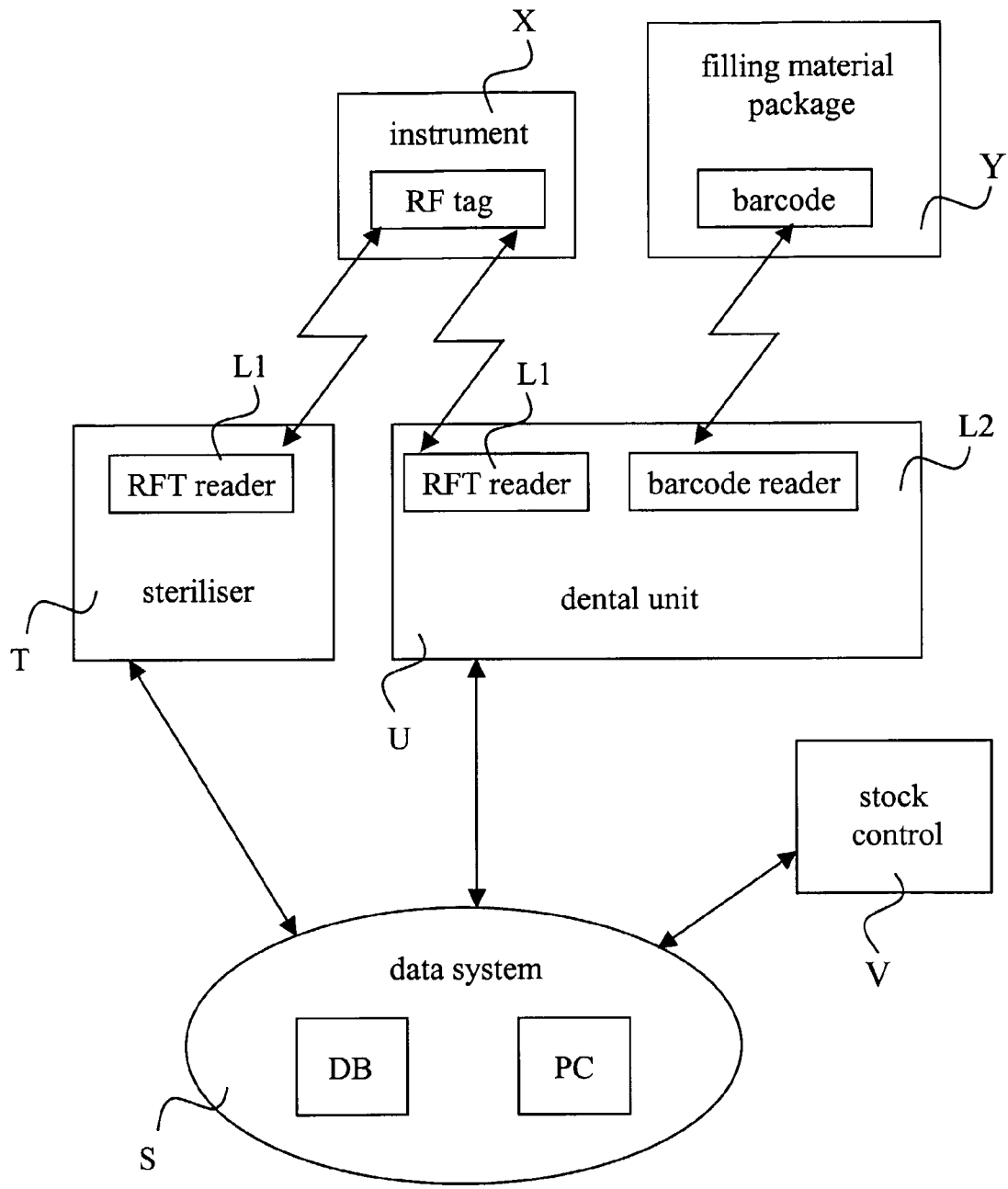
FIG. 1 illustrates an arrangement according to an embodiment of the invention.

FIG. 1 illustrates an arrangement according to an embodiment of the invention. It comprises a data system S and at least one device used in connection with dental care, which device may be, for example, a dental unit U or an instrument-sterilisation device T. Instruments X may be connected to the dental-care machine U. The instrument X may be, for example, an instrument for excavating, that is, for drilling a tooth, a light curer or an instrument for finishing a filled tooth or some other instrument related to a dental procedure. The data system S comprises one or more databases DB and a terminal PC. Connections inside the system S may be implemented, for example, by means of a local area network (LAN) and/or totally or partly as a wireless and/or mobile network. The dental-care-related device U, T and/or the terminal PC comprises a user interface and display means (not shown in FIG. 1) by means of which the data and/or messages related to dental procedures may be shown.

An arrangement according to an exemplary embodiment of the invention comprises at least one electronic sensor, reader device L1, L2, keyboard, camera or similar device by means of which data of the treatments carried out, the means and materials used for treatment and/or the operation parameters and their values relating to the means that were used may be registered. These devices may be physically integrated with the devices used in connection with dental care or with the data system or they may be separate devices. The reader devices L1, L2 are, for example, barcode readers or RFT (radio frequency tag) readers, and they comprise, for example, a serial connection for connecting the device either to the data system or, for example, to the dental unit.

FIG. 1 shows a situation according to an embodiment of the invention in which the RFT readers L1 are physically integrated with the dental unit U and the steriliser T, and in which the barcode reader L2 for reading the barcode of a filling material package Y is physically integrated with the dental unit U. The stock control V refers to, for example, the instrument and/or material storage. The sterilisation packages of instruments X are provided with RF identifiers which are readable by, for example, RFT readers L1 being located in connection with the dental-care machine U and steriliser T. The RFT identifier, that is, RF tag is a compact identifier the function of which is based on a radio-frequency field sent by the RFT reader, and the data stored in it may be changed. The instruments X themselves may have, for example, a barcode identifying their make, model and/or the individual instrument. The material packages Y are typically provided with barcode identifiers which are readable by, for example, the barcode reader L2 being located in connection with the dental unit U.

The architecture according to the embodiment of FIG. 1 is a simplified explanation of an embodiment of the invention, and it is well known by those skilled in the art that the arrangement may comprise also other devices, functions and structures, which there is no need to describe in detail in this context. A dental-care-related device means in this context the actual dental unit or a device used for sterilising instruments or some other device or equipment related to dental care. A dental unit is typically a multifunction unit which is used, for example, in connection with tooth excavation, filling and finishing of the filling.

Figure 2:
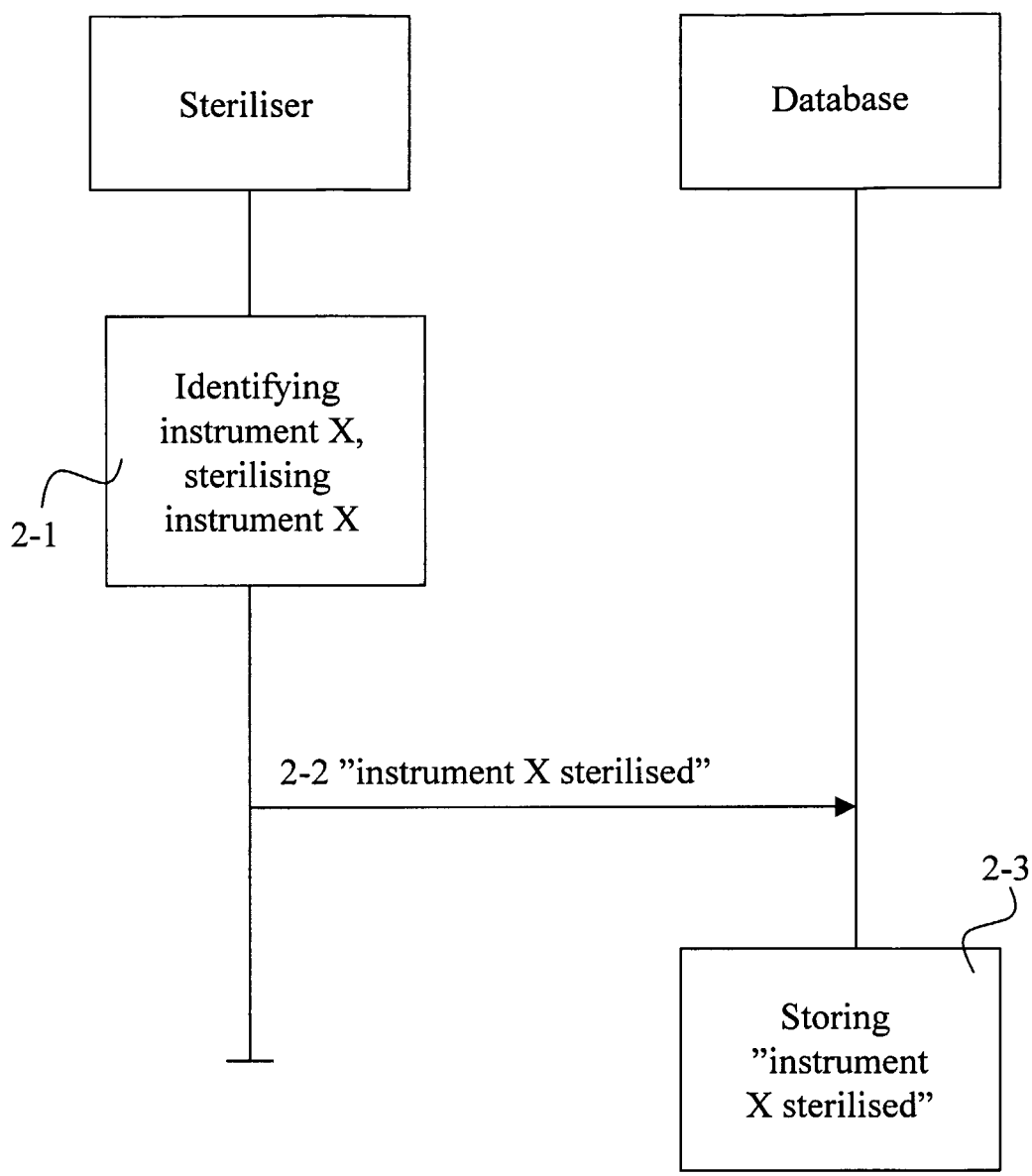
FIG. 2 illustrates signalling according to an embodiment of the invention in connection with instrument sterilisation.

FIG. 2 is a signalling diagram which illustrates an exemplary embodiment of the invention in connection with sterilisation of instruments X. The instruments may be sterilised one at a time in their own sterilisation packages or as prepared sets in sterilisation packages arranged for this purpose, or one may sterilise many similar instruments at a time so that after sterilisation the instruments will be packed into sterile packages, such as sterile heat-sealable bags. In item 2-1, the identifier being in connection with the instrument X is presented to the reader device L1 of the steriliser T, which reads the identifier. In addition to this or alternatively, the identifier in connection with the instrument sterilation package may be presented to the reader device L1. The instruments X are sterilised, and data is transmitted from the steriliser T in item 2-2 to the data system S of, for example, the point of time of sterilisation and of the fact that the instrument X in question is sterilised and packed in the sterilisation package in question. Thus, in item 2-3 data "instrument X sterilised at the point of time A" is stored in the database DB as the sterilisation status of instrument X. Also other data related to sterilisation may be stored, such as the changes of operation parameter values of the autoclave during sterilisation. After this, the instrument X is ready to be taken into storage or to be installed to the dental unit U.

Figure 3:
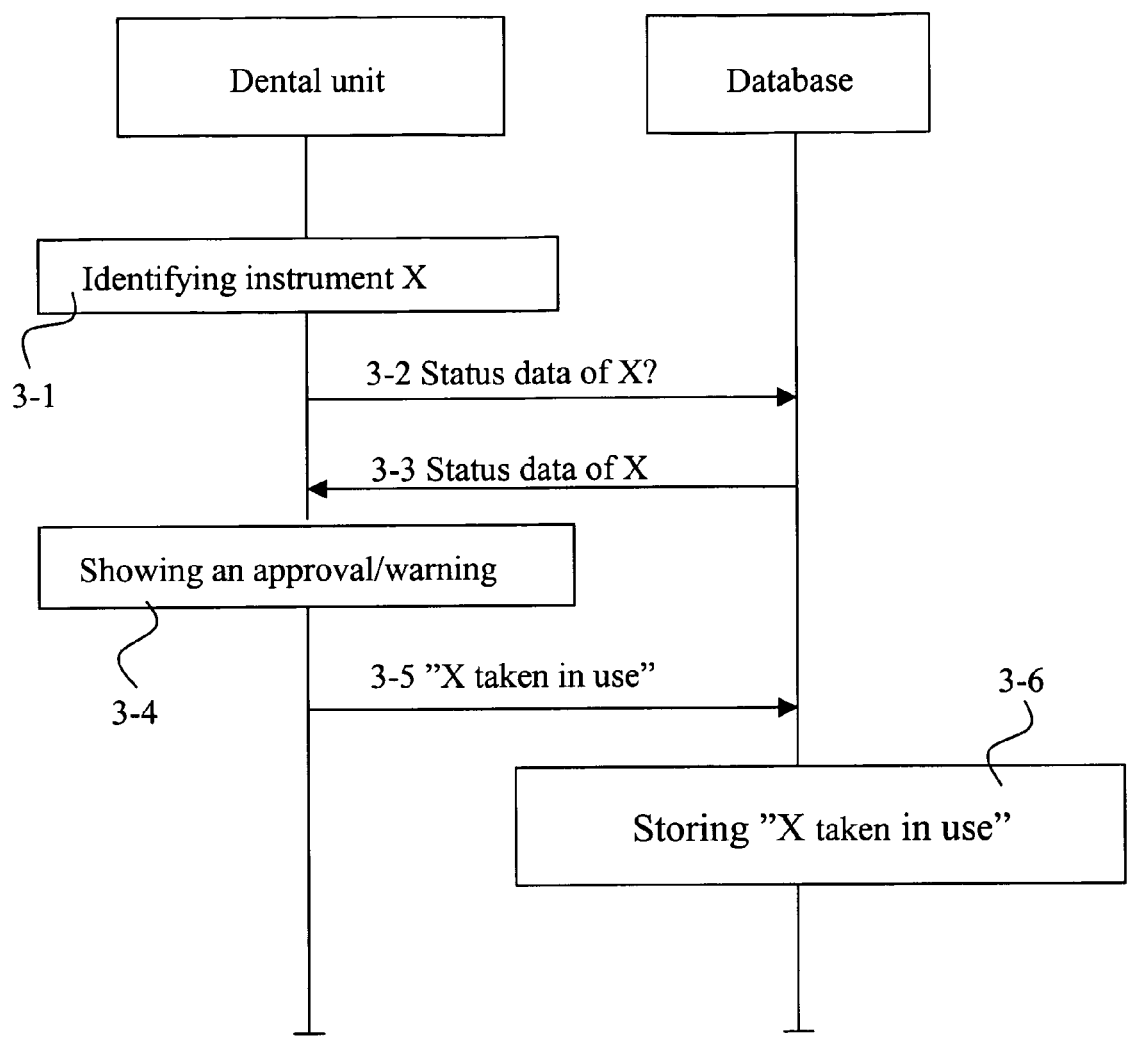
FIG. 3 illustrates signalling according to an embodiment of the invention in connection with starting use of an instrument.

FIG. 3 is a signalling diagram which illustrates a solution according to an exemplary embodiment of the invention in connection with start of use of an instrument X, that is, upon connecting the instrument X to a dental unit U. In item 3-1, the identifier of instrument X or its sterilisation package is presented to the reader device L1, L2 of the dental unit U, which identifier may be, for example, an RF tag of the sterilisation package of instrument X or a barcode of instrument X, and the reader device L1, L2 reads it. As a response to reading the identifier, the dental unit U asks 3-2 the data system after the status information of instrument X and/or of the sterilisation package in question, and the status information of instrument X or its sterilisation package stored in database DB is sent 3-3 from the data system to the dental unit U. If the status information of instrument X is in order (when the database DB has no information of instrument X being used or the sterilisation package being opened since the previous properly performed sterilisation), in item 3-4 a message is shown on the display incorporated with the dental unit U, such as "instrument data OK", and information that the instrument X was taken in use, and the point of time of it, is transmitted 3-5 to the data system. If status of the instrument or the sterilisation package is not appropriate, a corresponding warning or notice is shown in item 3-4. Alternatively, information that the instrument was taken in use may be transmitted to the data system not until it is acknowledged at the user interface in item 3-4 that the status data has been seen. When the data system has received a notice 3-5 of the instrument X having been taken in use, it stores the data of instrument X having been taken in use and, for example, of the fact that the instrument having been taken in use has been properly sterilised and maintained, in the database 3-6. The storing in question is preferably performed so that the data of the instrument status at that point of time in question is linked to the treatment history of the patient being treated, or the patient to be treated next.

Figure 4:
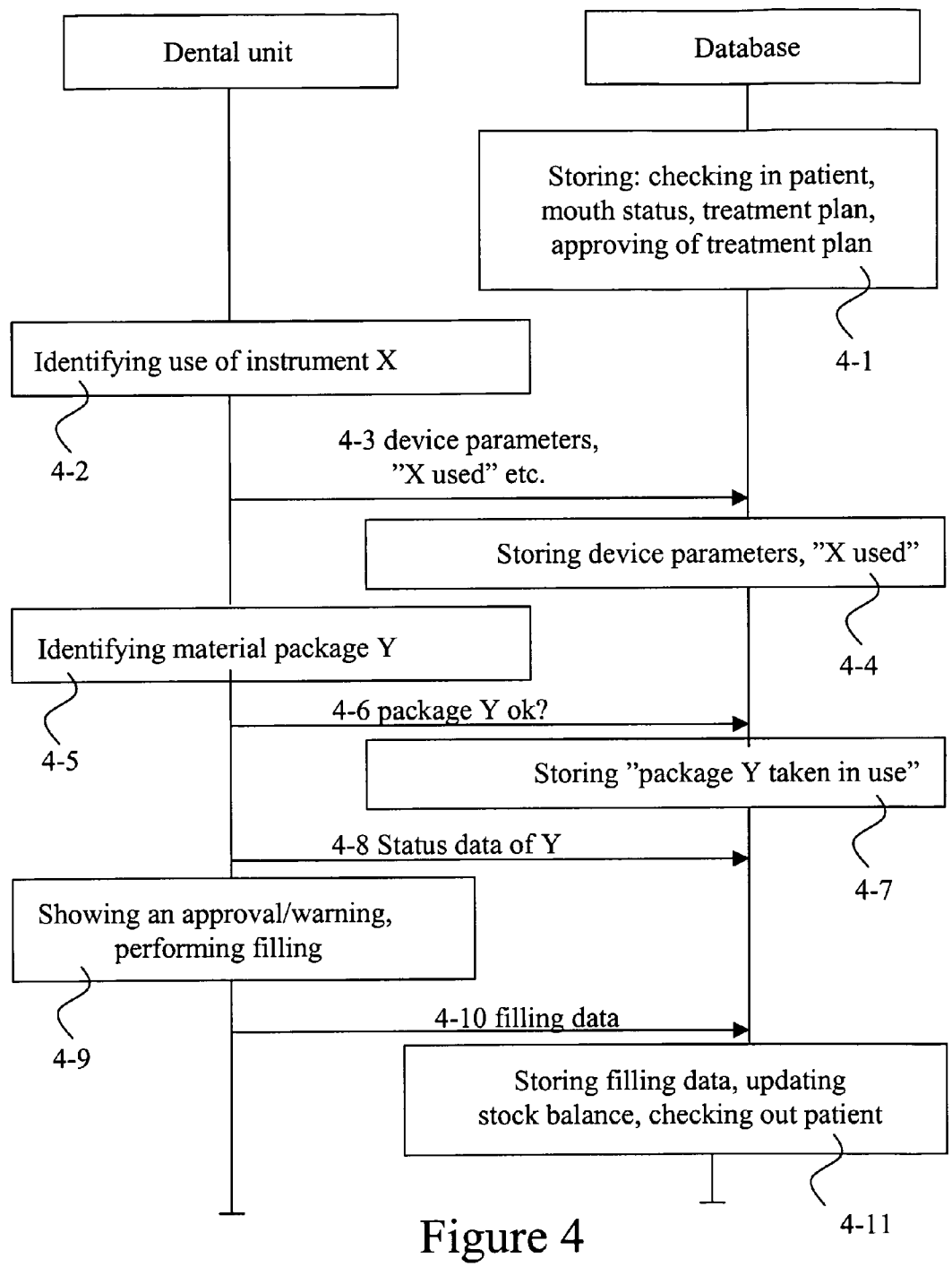
FIG. 4 illustrates signalling according to an embodiment of the invention in connection with dental procedures.

FIG. 4 is a signalling diagram which illustrates an exemplary embodiment of the invention in connection with a typical dental procedure. FIG. 4 shows a situation in which the basic information of a patient has been already entered in the patient database, a treatment time is reserved for the patient and possibly also the arrival of the patient to the clinic has been entered. In item 4-1, data is entered of, for example, start of the actual treatment session, of the mouth status survey of the patient made in this connection and of preparation of the treatment plan and of it having been approved by the patient. This data may be entered in the data system S, for example, by means of a microcomputer PC or a user interface arranged to the actual dental unit, and it is stored in the database DB. The data system S may have been arranged to point out if there exist errors or deficients in the data, for example, if some piece of information related to the patient, the tooth being treated or the treatment process is missing. A notice of storing the data may be transmitted (not shown in FIG. 4) to the dental unit U, and a message of the data being entered and stored in the electronic patient card (patient database) may be shown, for example, on the display connected to the dental unit. The data system may also be arranged to transmit (not shown in FIG. 4) to the dental unit a treatment plan and instrument data, such as control signals related to the hand piece and/or head used according to the treatment plan in question, based on which control signals, for example, the values of power or rotation speed to be used are shown as a response to receiving the signals in question in the dental unit.

In the embodiment according to FIG. 4, the procedure according to the treatment plan is removal of caries. Typically, at this stage the dental-care instruments X are connected to the dental unit U following the principles described in connection with FIG. 3. The arrangement preferably comprises a reminder function in a situation in which one attempts to use an instrument without entering or choosing data of whereto the procedure is targeted, such as data of the patient, the tooth to be treated and/or a certain surface of the tooth. Then, a corresponding notice may be shown on the display connected to the dental unit U. The dental procedure according to FIG. 4 may comprise drilling of the tooth, whereupon the control system of the dental unit identifies 4-2 the procedure, that is, in this case drilling. The identification of the procedure may be based on, for example, identifying lifting of the instrument X from the dental unit instrument table. Data of taking the instrument in use, and how it was used, is transmitted 4-3 to the patient database in which is stored 4-4, for example, data "properly at the point of time A sterilised instrument X was used at the point of time B for drilling tooth H of patient P by the drill operation parameter M, N, O values m, n, o". Operation parameter values to be stored may be, for example, drilling times, power and rotation speed, which data related to the drilling stage is thus transmitted 4-3 to be stored 4-4 in the database as a response to the use of drill in item 4-2.

Filling of a tooth is started by first identifying a material package Y in item 4-5. At this stage, the barcode identifier in the filling-material package Y is presented to a barcode reader L2 arranged in connection with the dental unit, the reader reads the barcode identifier and transmits its data to the dental unit U. The dental unit requests 4-6 from the data system S the data of the filling-material package Y in question, which data has been stored earlier in the database DB upon stocking, and possible prior use of the package ("package" may in this connection refer to, for example, a package including disposable ampoules or an individual package/ampoule). Data of opening and/or use of the package is updated 4-7 in the database DB. The status data of the package is transmitted 4-8 to the dental unit U. After this, a notice is shown 4-9 on the dental unit display of the use-by date, the storing situation of the filling material in question and/or, for example, a comment that there is also other material in the storage that could alternatively or even better be suited for use according to the treatment plan of the patient in question. Alternatively, the data in question may be shown on the terminal PC of the data system. In this context, the data system may also be configured to control the dental unit so that its instrument-specific operation parameters are set to preset values applicable in the filling function. In item 4-9, the cavity in the tooth is filled with filling material, and the material is cured by a light curer instrument. The curing is typically done in layers, in which case the filling comprises more than one filling and curing stages. Data of the operation parameters of these curing stages, such as the starting and ending time of each curing or the lengths of curing stages and possibly the power of the light-curing instrument, may be sent 4-10 from the dental unit to the data system S and be stored in the database DB already during the procedure, for example, as a response to the use of the light-curing instrument. Data on consumption of the filling material, such as the number of ampoules used, may also be stored in the database DB. Data of material consumption may be stored both in patient-specific data and stock control. Finally, the dental-care personnel registers that the treatment has been performed by, for example, an electronic signature, and the patient is checked out in item 4-11, whereupon the data of checking out and its time is stored in the database DB. Thus, one may easily acquire data from the data system later on that the patient P being treated at the point of time C so that a certain amount of filling material Y was used according to the treatment plan in question for filling the cavity, and that the material was cured in a certain number of stages using the light-curing instrument X by a certain power or powers, in which case, in light of this data, one may afterwards evaluate if the filling was properly performed.

Figure 5A:
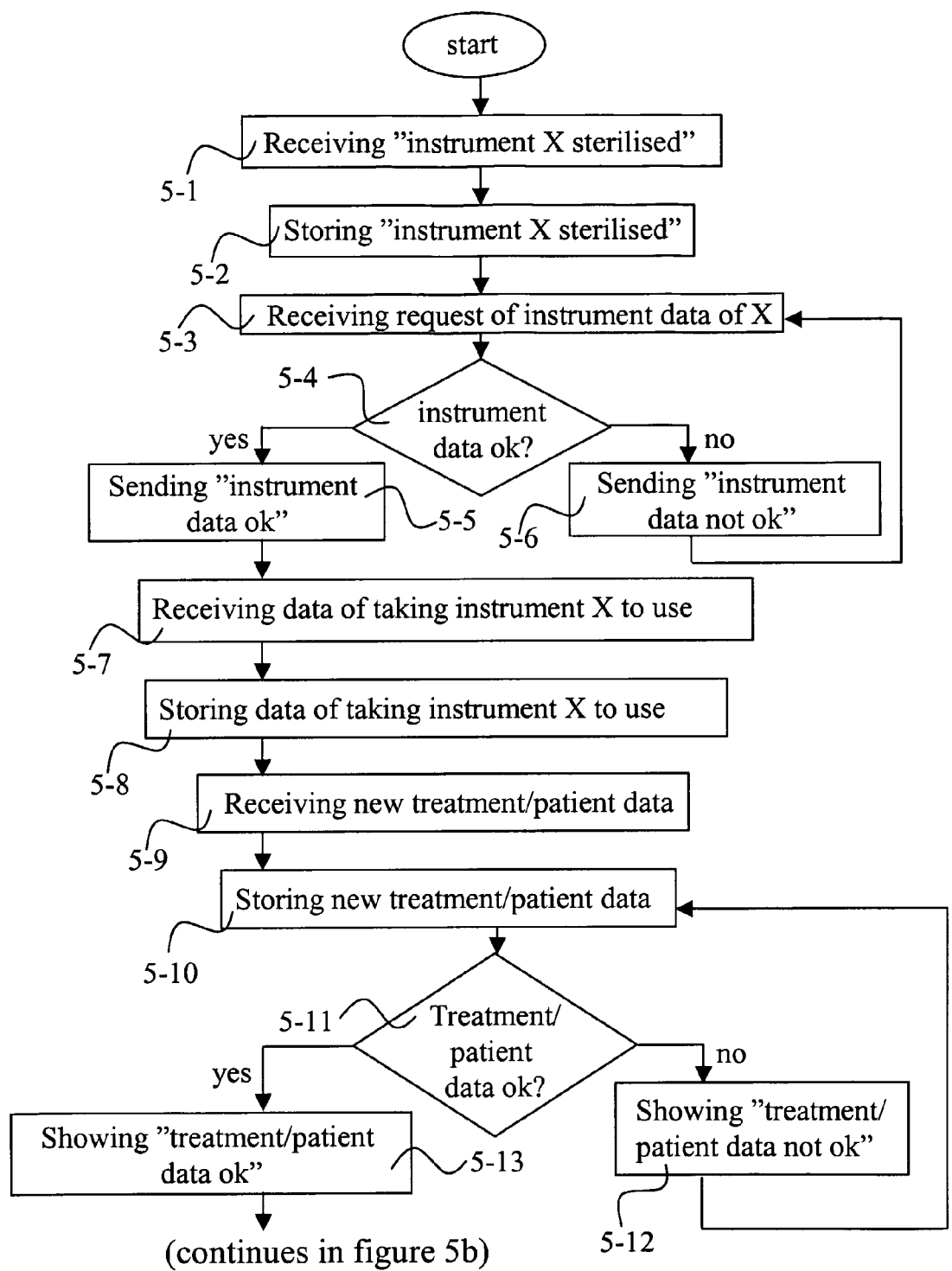
FIGS. 5a and 5b show a flow diagram illustrating a method according to an embodiment of the invention.

FIG. 5a is a flow diagram, which illustrates procedures according to an exemplary embodiment of the invention, performed in the data system S. In item 5-1, the data system S receives from the steriliser T data of sterilisation of an instrument X and, for example, the point of time of sterilisation and that the instrument X in question is packed in a certain sterilisation package. After this, in item 5-2 data, such as "instrument X sterilised at the point of time A", is stored in the data system database DB as the sterilisation status of instrument X. Also other data related to sterilisation may be stored in item 5-2, such as the changes of operation parameter values of the autoclave during sterilisation.

In item 5-3, the data system receives from the dental unit U a request of status data of an instrument X and/or a sterilisation package, and in item 54, the status data of instrument X or its sterilising package stored in database DB is retrieved to the dental unit U. If the status data of the instrument X is in order (when the database DB, for example, has no data of the instrument X being used or the sterilising package being opened since the previous properly performed sterilisation), a notice is transmitted 5-5 to the dental unit, such as "instrument data OK". If the status of the instrument or the sterilisation package is not appropriate, a corresponding warning or notice is transmitted 5-6 to the dental unit. In such a case, the dental-care personnel should check if it seems that there is uncertainty of the sterility of the instrument, and, if required, replace the instrument with another one. In item 5-7, data of taking instrument X to use and the point of time it was done is received. When the data system has received a notice of taking the instrument X to use, it stores 5-8 in the database DB the data of taking the instrument X to use and, for example, of the fact that the instrument that was taken to use has been properly sterilised and maintained.

In item 5-9, data is received of start of the actual treatment session, of the survey of the mouth status of the patient and preparation of the treatment plan and having it approved by the patient made in connection with it. In item 5-10, the data in question is stored in the database DB. The data system S may have been arranged to check in item 5-11 if there are errors or defects in the data, for example, if data of the patient, the tooth to be treated or the treatment process is missing or if data is entered in the data system or if data of whereto the procedure is directed has been chosen, such as data of the patient, tooth to be treated and/or the surface of the tooth to be treated. A warning or notice of possible errors or defects is sent in item 5-12 to the dental unit or the terminal PC. Alternatively, in item 5-13, a notice of the data being properly entered and stored is transmitted to the dental unit U. After this, the process of FIG. 5a continues, for example, in a manner as described in connection with FIG. 5b below.

Figure 5B:
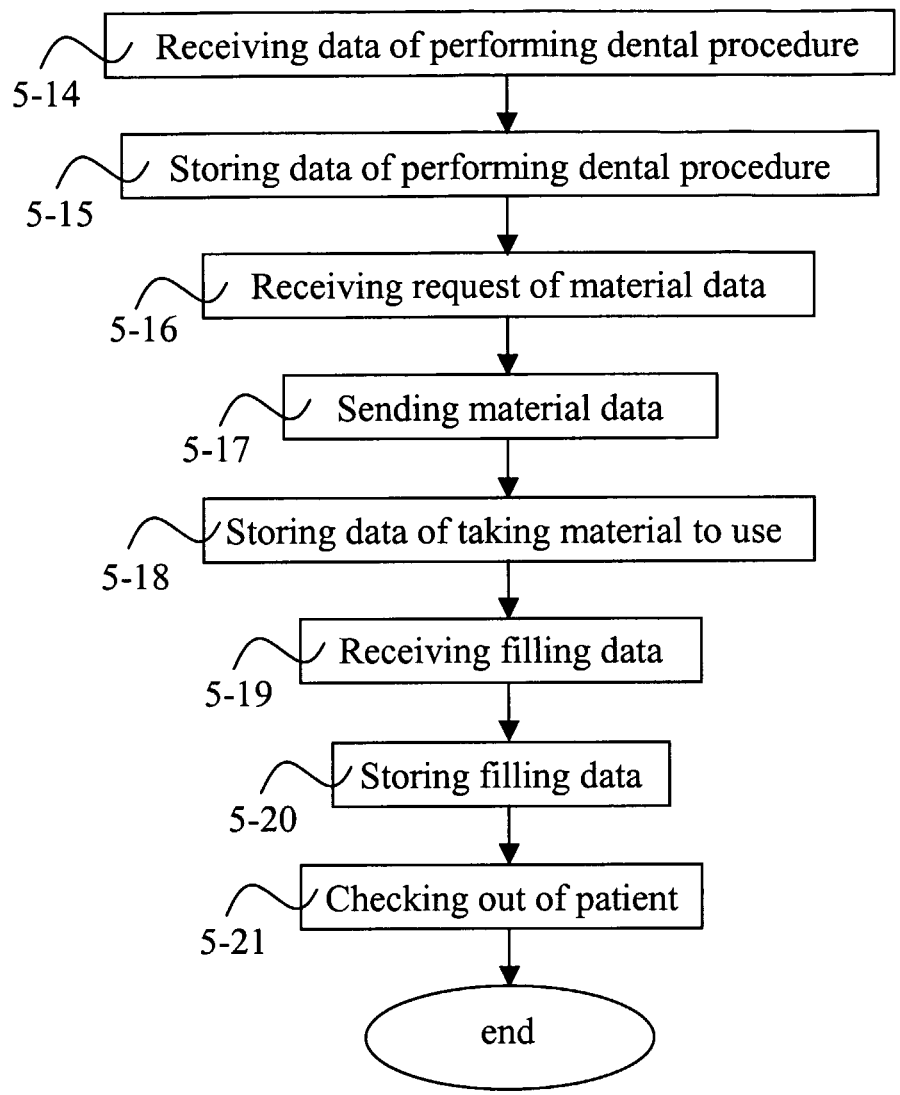

FIG. 5b is a flow diagram, which illustrates procedures according to an exemplary embodiment of the invention, performed in the data system S. The process of FIG. 5b is a continuation of, for example, items described in connection with FIG. 5a above. In item 5-14, data is received from the dental unit control system of what kind of dental procedure, for example, drilling, was performed by the dental unit U and data of this is stored 5-15 in the database DB, in which is stored, for example, data "properly at the point of time A sterilised instrument X was used at the point of time B for drilling tooth H of patient P by the drill operation parameter M, N, O values m, n, o".

In item 5-16, a request is received from the dental unit concerning filling-material package Y data which has been stored in the database DB earlier upon stocking the package and upon its possible prior use. The status data of the package is transmitted 5-17 to the dental unit U, such as data of the use-by date, storage situation of the filling material in question and/or, for example, a comment that there is also other material in the storage which could alternatively or even better be suited for use according to the treatment plan of the patient in question. Data of opening and/or use of the package is updated 5-18 in the database DB. The data in question may also be shown on the terminal PC of the data system. The filling of the tooth is performed typically in layers, in which case the filling comprises more than one filling and curing stage. Data of the operation parameters of these curing stages, such as the starting and ending time of each curing or the lengths of curing stages and possibly the power of the light-curing instrument, are received 5-19 from the dental unit and stored 5-20 in the database DB already during the procedure. Data of consumption of the filling material, such as the number of ampoules used, may also be stored in the database DB. Data of material consumption may be stored both patient-specifically and in the stock control. Finally, data of checking out of the patient is received and stored in item 5-21.

Items and signallings described in FIGS. 2, 3, 4, 5a, and 5b may also be implemented in other order than described here, and there may be other functions between them or only part of the functions may be performed. The items and signalling messages described may also include other than the data presented, or they may include only part of the data presented above. For example, only part of the items described in FIGS. 5a and 5b may be performed, for example, items 5-1, 5-2, 5-7, 5-8, 5-9, 5-10, 5-14, 5-15, 5-18, 5-19, and 5-20. The procedures may also be repeated more than once, in case needed.

Figure 6A:
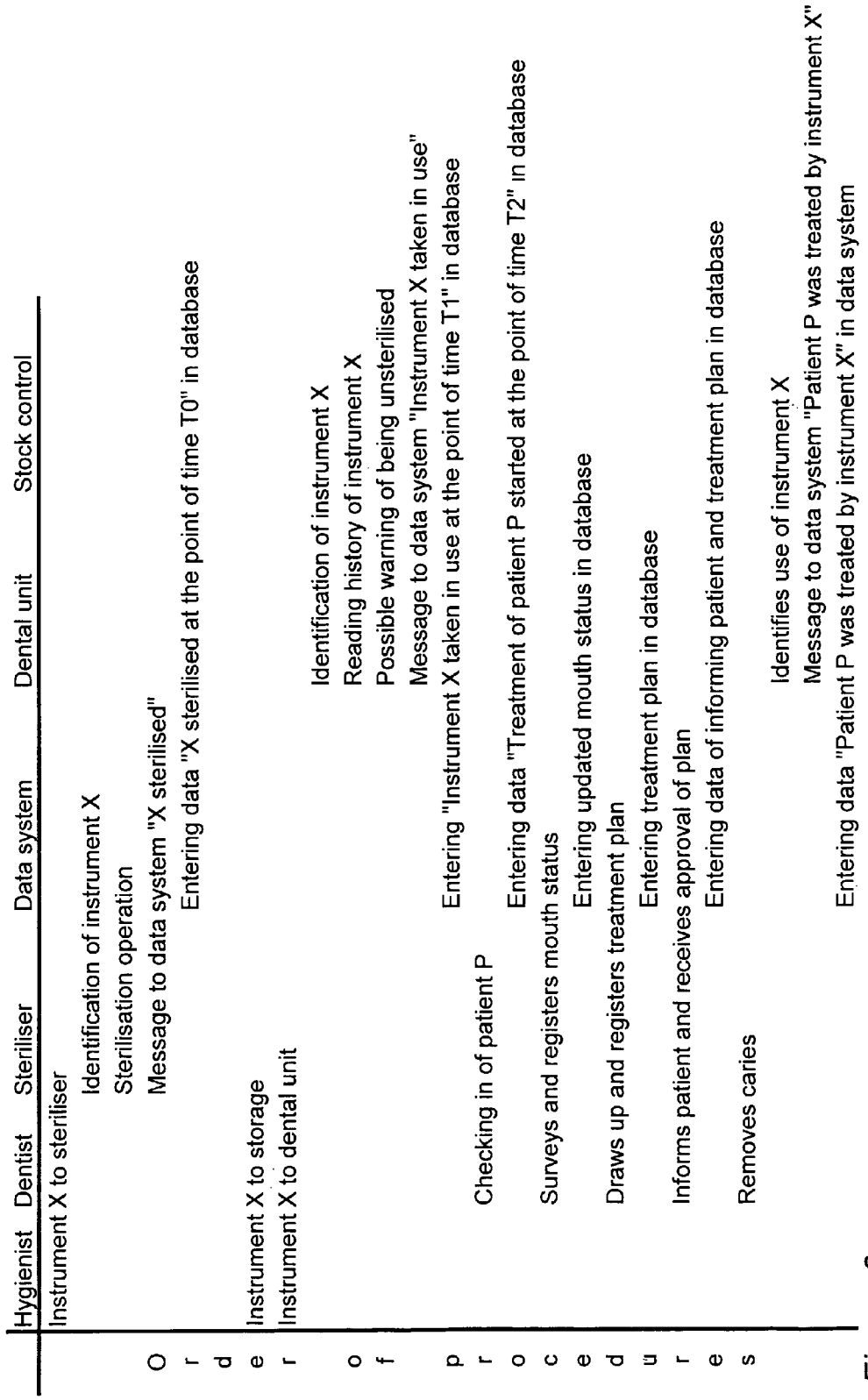
FIG. 6a shows a table illustrating a method according to an embodiment of the invention.

FIGS. 6a and 6b describe by way of examples how the elements and equipment related to dental-care situations function in an environment according to the invention in relation to each other in connection with some procedures related to dental care.

In this patent application, by the term "store" is meant short- or long-term storing of information related to dental-care events depending on what is expedient in each case from the viewpoint of assurance of legal protection of the patient and the dental clinic or control of the dental unit in contemplation of later utilisation of the data and quality assurance of dental-care work. The information may be stored in an "electronic patient card" or otherwise controllably so that it can be searched from the data system when required and may be linked to the correct patient, care personnel, device, treatment event and/or date and time etc. Thus, information of the item of the procedure will be stored in the data system item-specifically. The item may be, for example, a dental-care instrument, material used in dental care or its package, a patient card or a certain tooth or a certain tooth surface of the patient.

Data transmission and storing may take place so that when a dental-care-related device is used, data is transmitted electronically e.g. from the control system of the dental-care-related device to a data system, whereat data of, for example, the device and instruments that are being used, and durations of their use and their operation parameter values will be stored in the data system. This data is transmitted and stored according to the invention from, for example, the dental unit control system the software pertaining to which "knowing" and "deducting" different items related to the dental unit functions, such as which instrument is being used, how long it is used, which variables the use of the instrument requires and which are the current (control) values of the respective operation parameters etc. For example, when the operating system controls power of the light-curing instrument controlled via the foot controller of the dental unit, the software knows that the light-curing instrument is now on and may calculate its operating time.

When one arranges into connection with a dental-care-related device at least one such a device, for example, an electronic reader device, a keyboard, a sensor, a camera or a similar device via which it is possible to receive data of the dental procedures performed, the treatment instruments, materials and/or the operation parameter values of devices and/or instruments used in treatment in electronic format, one may also store such a data in a desired location. For example, by means of an electronic reader device, such as a barcode or RFT reader, a dentist or dental hygienist may read and store a proper barcode identifier or other identifier readable with a reader device directly in connection with the treatment session. The identifier may be, for example, a barcode on the sterilisation package of a dental-care instrument or on a filling material package. In addition to thus enabling immediate storing data of, for example, the filling material used in connection with the treatment event, one will be able to check at the same time from the data system that the material package in question is not e.g. out-of-date or that the material itself is not inapplicable for the planned use for some other reason.

According to an embodiment of the invention, information related to dental-care events comprises at least one of the following data related to dental-care instruments and/or their use: data of the type of a dental-care instrument, identification data of the dental-care instrument, maintenance status data of the dental-care instrument, sterilisation status data of the dental-care instrument, data of the point of time of sterilisation of the dental-care instrument, data of connecting the dental-care instrument to the dental unit, data of taking the dental-care instrument in use in connection with a treatment event, data of the point of time when the dental-care instrument was taken in use, data of operation parameter values of the dental-care instrument during the dental treatment event comprising data of operation time, rotation speed and/or power used, data of disconnecting the dental-care instrument from the dental unit, data of the point of time of disconnection of the dental-care instrument, data of starting and ending the sterilisation treatment of the dental-care instrument, data of the starting and ending time of the sterilisation treatment of the dental-care instrument, and sterilisation process parameter values during sterilisation.

According to an embodiment of the invention, information related to dental-care events comprises at least one of the following data related to dental-care materials and/or their use: data of material used in dental treatment, data of the point of time of arrival of the material package used in dental treatment to the clinic, identifying data of the material package and/or its manufacturing lot, data of the use-by date accordant with the material package, data of opening the material package, data of the point of time of opening of the material package, data of the point of time of use of the material, data of the amount of material used.

According to an embodiment of the invention, information related to dental-care events comprises a treatment plan of a patient, data of performing a certain treatment procedure, and/or data of the point of time the procedure was performed.

According to an embodiment of the invention, the data system may also be arranged to transmit, as a response to storing a treatment plan of a patient, to the dental unit control signals, which relate to treatment plan and instrument data such as the hand piece and/or head, for example, for presetting the values of power or rotation speed to be used in the dental unit.

According to an embodiment of the invention, the data system may be arranged to transmit, as a response to taking a filling material package to use, to the dental unit control signals based on which instrument-specific operation parameters will be set to the preset values applicable in the filling procedure.

According to an embodiment of the invention, data will be sent from the data system to the stock control V of the material packages and/or instruments that have been used, whereby it is possible to update the material and/or instrument stock balance in the stock control. In an arrangement according to the invention, the stock control may be configured to warn if the amount of certain material in the storage is below a predetermined amount, whereby an order for additional material may be placed in time.

According to an embodiment of the invention, an instrument is provided with a non-volative memory (EEPROM, electrically erasable programmable read-only memory) in which is stored identifying data of the instrument, which data may be read by a dental-care-related device U, T.

A data arrangement implementing the functionality according to the present invention comprises, in addition to that of the prior-art, means for identifying and storing events item-specifically. To be more precise, it comprises means for implementing at least one of the embodiments described above. Personal computers or terminals and database servers today comprise processors and memory, which may be utilised in operations according to the invention. All changes and configurations required to implement the invention may be performed as added or updated software routines, with application-specific integrated circuits (ASICs) and/or by configuring an existing system in other ways. The software/software routine(s) may be stored on any kind of data storage device, which is readable by a computer.

By means of the invention, it is possible to improve the quality assurance of dental care when the data related to different procedures of the treatment may be stored extensively and directly already in connection with the treatment event. For example, if a patient claims having caught hepatitis from the dental clinic, one will be able to verify from the data system if the instruments used in connection with the treatment event have been properly sterilised. On the other hand, if the manufacturer of filling material notifies that a certain material lot has perished, one obtains data from the data system of those patients whose fillings need to be replaced. An arrangement according to the invention may be utilised also in other clinic functions, such as stock control. In addition, entering and storing data has been advantageously arranged as automatic as possible, whereby the care personnel may spend as little time as possible for manual entering and storing of different data. In addition, data stored in the data system may be utilised in controlling the dental unit, in addition to control commands given via user interface of the dental unit, such as push buttons and foot control.

It is well known by those skilled in the art that upon advancing of technology, the basic idea of the invention may be implemented in many different ways. The invention and its embodiments are thus not limited to the examples described above but may vary within the scope of the patent claims.

The invention claimed is:

1. Data arrangement for a dental-care environment, for use during a dental procedure, said environment including at least one dental-care instrument (X), a dental unit (U) comprising an instrument table, said dental unit (U) being configured to control the operation of said at least one dental-care instrument during the dental procedure, a data system (S) and a data communication arranged between the dental unit (U) and the data system (S), said data arrangement comprising:
   means for identifying during the dental procedure the taking of said at least one dental-care instrument (X) from said instrument table to use in the dental procedure;
   means for transmitting at least one value of at least one operation parameter of said at least one dental-care instrument (X) during the procedure to said data system (S) as a response to the identification by said identifying means of the taking of said at least one dental-care instrument (X) from said instrument table; and
   means for storing said transmitted at least one value of at least one operation parameter in the data system (S) during the dental procedure item-specifically, said item being at least one of said at least one dental-care instrument (X), a patient, a certain tooth of a patient, and/or a certain tooth surface of a patient.

2. Arrangement according to claim 1, wherein the taking of said at last one dental-care instrument (X) to use during the dental procedure is followed by a treatment event the target of which being a patient; and
   the means for storing have been arranged to store information related to the treatment event patient-specifically.

3. Arrangement according to claim 1, wherein the dental unit (U) comprises means for receiving information related to the taking of said at last one dental-care instrument (X) to use during the procedure.

4. Arrangement according to claim 1, wherein the information related to the taking of said at last one dental-care instrument (X) to use during the dental procedure further comprises at least one of the following data: data of the type of dental-care instrument (X), identification data of the dental-care instrument (X), maintenance status data of the dental-care instrument (X), sterilisation status data of the dental-care instrument (X), point of time of sterilisation of the dental-care instrument (X), data of connecting the dental-care instrument (X) to the dental unit (U), data of taking the dental-care instrument (X) to use in connection with a treatment event, data of the point of time the dental-care instrument (X) was taken to use, and wherein said at least one value of at least one operation parameter during the dental procedure comprises data of operation time, rotation speed and/or power used, data of disconnecting the dental-care instrument (X) from the dental unit (U), data of disconnection time of the dental-care instrument (X) from the dental unit (U), data of performing a certain treatment procedure, and/or data of the point of time of performance of a certain treatment procedure.

5. Arrangement according to claim 1, wherein the means for identifying the taking of said at last one dental-care instrument (X) to use during the procedure comprise an electronic reader device.

6. Arrangement according to claim 1, wherein the data system (S) further comprises a user interface and a display means connected with it; and
   the data system (S) is configured for transmitting to the display means information stored in the data system (S) and/or messages based on said information.

7. Arrangement according to claim 1, wherein the data system (S) is configured for transmitting to the dental unit (U) control data relating to a treatment plan and/or at least one dental care instrument (X); and the dental unit (U) has been arranged to be controlled according to said control data as a response to receiving said control data.

8. A method for maintaining an electronic dental-care register for a dental-care environment during a dental procedure, the dental-care environment including at least one dental-care instrument (X), a dental unit (U) comprising an instrument table, said dental unit (U) being configured to control the operation of said at least one dental-care instrument (X) during a dental procedure, and a data system (S), comprising the steps of:

forming a data transmission communication between the dental unit (U) and the data system (S);

identifying during the dental procedure the taking of said at least one dental-care instrument (X) from the instrument table to use in the dental procedure;

transmitting at least one value of at least one operation parameter of said at least one dental-care instrument (X) during the dental procedure to said data system (S) as a response to the identification of the taking of said at least one dental-care instrument (X) from said instrument table in said identifying step;

receiving said transmitted at least one value of at least one operation parameter in the data system during the dental procedure; and storing said received at least one value of at least one operation parameter during the dental procedure item-specifically, said item being at least one of said at least one dental-care instrument (X), a patient, a certain tooth of a patient, a certain tooth surface of a patient.

9. Method according to claim 8, wherein the at least one operation parameter of said at least one dental-care instrument (X) is stored patient-specifically.

10. Method according to claim 8, wherein the at least one operation parameter of said at least instrument is stored instrument-specifically.

11. Method according to claim 8, including the additional steps of:

transmitting identification data of an individual dental-care instrument (X) taken for use in the dental procedure;

comparing the identification data with a treatment plan of a patient who is the object of the dental procedure and/or with status data of the dental-care instrument (X) taken for use:.

detecting whether the dental-care instrument (X) is unsterilised or does not correspond to the treatment plan and expressing the detection as a response to detecting an unsterilised dental-care instrument (X) or a dental-care instrument not corresponding to the treatment plan.

12. Method according to claim 8, wherein information related to the taking of said at last one dental-care instrument (X) to use during the dental procedure is stored in a patient database of the dental clinic data system (S).

13. Method according to claim 8, wherein the method further comprises the steps of:

as a response to identifying taking the at least one dental-care instrument (X) to use, transmitting data of taking said instrument (X) to use and storing said data in the data system (S) instrument-specifically and patient-specifically, and further transmitting data of a dental procedure performed by said dental-care instrument (X) and storing the data in the data system patient-specifically.

14. A dental-care-related device for use in a dental-care environment during a dental procedure, said dental-care environment including at least one dental-care instrument (X) and a data system (S), said dental-care-related device comprising:

means for forming a data transmission communication with said data system (S) of said dental-care environment;

a dental unit (U) configured to control operation of said at least one dental-care instrument (X) during the dental procedure;

means for identifying the taking of said at least one dental-care instrument for use in the dental procedure;

means for transmitting at least one value of at least one operation parameter of said at least one dental-care instrument (X) during the dental procedure to the data system (S) as a response to the identification by said identifying means of the taking of said at last one dental-care instrument (X) for use in the dental procedure; and means included in said data system (S) for storing said at least one value of at least one operation parameter of said at least one dental-care instrument (X) during the dental procedure item-specifically.

15. Software product for a dental-care environment for use during a dental procedure, said dental-care environment including at least one dental-care instrument (X), a dental unit (U) configured to control operation of said at least one dental-care instrument (X) during the dental procedure, and a data system (S), said software product comprising a program stored on program storage means which is readable by a computer, wherein when the program is executed it performs:

a first routine by which a data transmission communication between the dental-care related device (U) and the data system (S) is formed;

a second routine by which the taking of said at least one dental-care instrument (X) for use in the dental procedure is identified; and a third routine by which at least one value of at least one operation parameter of said at least one dental-care instrument (X) during the dental procedure is transmitted from the dental unit (U) to the data system (S) as a response to the identification of the taking of said at least one dental-care instrument (X) for use in the dental procedure in the performance of said second routine.

16. Software product according to claim 15, wherein said program comprises a routine for running a method for maintaining an electronic dental-care register for a the dental-care environment in a data arrangement, wherein said at least one operation parameter of said at least one dental-care instrument (X) is received in the data system (S); and said at least one operation parameter of said at least one dental-care instrument (X) is stored in the data system (S) item-specifically.

17. Software product for a dental-care environment for use during a dental procedure, said dental-care environment including at least one dental-care instrument (X), a dental unit (U) configured to control operation of said at least one dental-care instrument (X) during the dental procedure, and a data system (S), said software product comprising a program stored on program storage means which is readable by a computer, wherein when the program is executed it performs:

a first routine by which at least one value of at least one operation parameter of said at least one dental-care instrument (X) during the dental procedure is received in the data system (S) as a response to the taking of said at least one dental-care instrument (X) for use in the dental procedure; and a second routine by which said at least one value of at least one operation parameter of said at least one dental-care instrument (X) which is received in said data system in the performance of said first routine is stored in the data system, item-specifically.

18. Software product according to claim 17, wherein said program comprises a routine for running a method for maintaining an electronic dental-care register for the dental-care environment in a data arrangement, wherein a data transmission communication is formed between the dental unit (U) and the data system (S); and said at least one operation parameter of said at least one dental-care instrument (X) is stored in the data system (S) item-specifically.

* * * * *